(12) United States Patent
Kim et al.

(10) Patent No.: US 11,571,181 B2
(45) Date of Patent: Feb. 7, 2023

(54) ULTRASOUND IMAGING APPARATUS

(71) Applicant: SAMSUNG MEDISON CO., LTD., Gangwon-do (KR)

(72) Inventors: Nam Yun Kim, Seoul (KR); Jong-Moon Kim, Seoul (KR); Kyeong Gu Woo, Suwon-si (KR); Sim Gwan Jeong, Seoul (KR); Wan Ki Kim, Seoul (KR); Dai Un Park, Yongin-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 561 days.

(21) Appl. No.: 16/606,020

(22) PCT Filed: Feb. 6, 2018

(86) PCT No.: PCT/KR2018/001591
§ 371 (c)(1),
(2) Date: Oct. 17, 2019

(87) PCT Pub. No.: WO2018/194246
PCT Pub. Date: Oct. 25, 2018

(65) Prior Publication Data
US 2020/0037988 A1    Feb. 6, 2020

Related U.S. Application Data

(60) Provisional application No. 62/486,600, filed on Apr. 18, 2017.

(30) Foreign Application Priority Data

Nov. 3, 2017  (KR) ........................ 10-2017-0145801

(51) Int. Cl.
*A61B 8/00* (2006.01)
*F16C 19/26* (2006.01)

(52) U.S. Cl.
CPC ................ *A61B 8/44* (2013.01); *F16C 19/26* (2013.01); *F16C 2233/00* (2013.01)

(58) Field of Classification Search
CPC . A61B 8/4405; A61B 8/46; A61B 2560/0437; F16C 13/006; F16M 11/28
See application file for complete search history.

(56) References Cited

U.S. PATENT DOCUMENTS

| 5,129,397 A | 7/1992 | Jingu et al. |
| 2006/0104553 A1* | 5/2006 | Faust ................... F16C 29/123 384/49 |

(Continued)

FOREIGN PATENT DOCUMENTS

| CN | 101868167 A | 10/2010 |
| CN | 104902822 A | 9/2015 |

(Continued)

OTHER PUBLICATIONS

Extended European Search Report dated Mar. 11, 2020 issued in European Patent Application No. 18787902.8.

(Continued)

*Primary Examiner* — Bill Thomson
*Assistant Examiner* — Aminah Asghar
(74) *Attorney, Agent, or Firm* — Morgan, Lewis & Bockius LLP

(57) ABSTRACT

The present disclosure relates to an ultrasonic imaging apparatus that has a tolerance for easy assembly and reduces shaking and noise by reducing the tolerance after assembly. The ultrasonic imaging apparatus includes a main body, a probe connected to the main body to irradiate and receive ultrasonic waves and to transmit the ultrasonic signals to the main body, a control panel configured to control the main body or the probe, and a moving device configured to connect the control panel and the main body and to move the (Continued)

control panel with respect to the main body in the upward and downward directions, wherein the moving device includes a housing fixed to the main body, a moving member configured to be movable with respect to the housing in the upward and downward directions, and a regulating bearing installed in the housing and configured to assist the upward and downward movement of the moving member by coming into rolling contact with the moving member and to regulate a gap with the moving member.

13 Claims, 12 Drawing Sheets

(56) References Cited

U.S. PATENT DOCUMENTS

| | | | |
|---|---|---|---|
| 2010/0244454 | A1 | 9/2010 | Loeschner et al. |
| 2011/0184285 | A1* | 7/2011 | Danli .................... A61B 8/462 600/437 |
| 2011/0224544 | A1* | 9/2011 | Ahn .................... A61B 8/4405 600/437 |
| 2012/0091299 | A1 | 4/2012 | Levine |
| 2012/0306249 | A1 | 12/2012 | Jung |
| 2013/0251112 | A1* | 9/2013 | Taku .................... A61B 5/0091 378/208 |
| 2015/0105661 | A1* | 4/2015 | Woo .................... A61B 8/14 600/437 |
| 2016/0193890 | A1 | 7/2016 | Dobre et al. |

FOREIGN PATENT DOCUMENTS

| | | | | |
|---|---|---|---|---|
| CN | 204673231 | U | | 9/2015 |
| EP | 2241255 | A2 | | 10/2010 |
| GB | 2507738 | A | * | 5/2014 ........... F16M 11/046 |
| JP | 2005-205200 | A | | 8/2005 |
| JP | 2005-342056 | A | | 12/2005 |
| JP | 2007-6968 | A | | 1/2007 |
| JP | 2017-006476 | A | | 1/2017 |
| KR | 10-2010-0136865 | A | | 12/2010 |
| KR | 10-2012-0023210 | A | | 3/2012 |
| KR | 10-1233302 | B1 | | 2/2013 |
| KR | 101233302 | | * | 2/2013 |

OTHER PUBLICATIONS

International Search Report issued in International Application No. PCT/KR2018/001591 dated May 8, 2018, with English translation.
Written Opinion issued in International Application No. PCT/KR2018/001591 dated May 8, 2018.
Chinese Office Action dated Jan. 19, 2022 issued in Chinese Patent Application No. 201880025853.7 (with English translation).
Chinese Office Action dated Jun. 14, 2022 issued in Chinese Patent Application No. 201880025853.7 (with English translation).
Korean Office Action dated Sep. 16, 2022 issued in Korean Patent Application No. 10-2017-0145801 (with English translation).

* cited by examiner

ULTRASOUND IMAGING APPARATUS

CROSS REFERENCE TO RELATED APPLICATIONS

This application is the U.S. National Phase under 35 U.S.C. § 371 of International Application No. PCT/KR2018/001591 filed on Feb. 6, 2018, which claims the benefit of U.S. Provisional Application No. 62/486,600 filed on Apr. 18, 2017 and Korean Application No. 10-2017-0145801 filed on Nov. 3, 2017, the entire contents of each are hereby incorporated by reference.

TECHNICAL FIELD

The present disclosure relates to an ultrasonic imaging apparatus, and more particularly, to an ultrasonic imaging apparatus capable of moving a control panel up and down.

BACKGROUND ART

An ultrasonic imaging apparatus is an apparatus that irradiates an ultrasonic signal from a body surface of a target toward a target site in the body and obtains an image of a monolayer or blood flow of soft tissue without invasion by using information of a reflected ultrasonic signal (ultrasonic echo signal).

The ultrasonic imaging apparatus has been widely used for diagnosis of the heart, abdomen, urinary system and obstetrics because it is small, inexpensive, real-time displayable, easy to use, and has a High level of safety because there is no radiation exposure, compared to other imaging apparatuses such as an X-ray diagnostic apparatus, an X-ray CT scanner (Computerized Tomography Scanner), an MRI (Magnetic Resonance Image) and a nuclear medicine diagnostic apparatus.

The ultrasonic imaging apparatus includes an ultrasonic probe for transmitting an ultrasonic signal to a target object to obtain an ultrasonic image of the target object and receiving an ultrasonic echo signal reflected from the target object, and a main body for generating an image of the inside of the target object by using the ultrasonic echo signal received from the ultrasonic probe.

The ultrasonic imaging apparatus may include a control panel provided for a user to control the ultrasonic imaging apparatus. It is preferred that the control panel is provided to be movable up and down according to the height or posture of the user. For the upward and downward movement of the control panel, the ultrasonic imaging apparatus may include a control panel vertical moving device.

In general, parts having structures fitted to each other have assembly tolerances for ease of assembly.

A conventional moving device requires a tolerance for assembly, as in general assembly structures. The assembly tolerance is necessary to assemble, but there is a problem that shake and noise due to the assembly tolerance occurs after assembly is completed.

In addition, the conventional moving device uses a structure such as a rail that requires a separate processing or requires a precise design, thereby increasing the production cost.

DISCLOSURE

Technical Problem

The present disclosure is directed to providing an ultrasonic imaging apparatus with improved user convenience due to reduced shaking and noise when a control panel is moved up and down.

Further, the present disclosure is directed to providing an ultrasonic imaging apparatus capable of precise movement by reducing a clearance while having a simple structure.

Technical Solution

One aspect of the present disclosure provides an ultrasonic imaging apparatus including a main body, a probe connected to the main body to irradiate and receive ultrasonic waves and to transmit the ultrasonic signals to the main body, a control panel configured to control the main body or the probe, and a moving device configured to connect the control panel and the main body and to move the control panel with respect to the main body in the upward and downward directions, wherein the moving device includes a housing fixed to the main body, a moving member configured to be movable with respect to the housing in the upward and downward directions, and a regulating bearing installed in the housing and configured to assist the upward and downward movement of the moving member by coming into rolling contact with the moving member and to regulate a gap with the moving member.

The regulating bearing may include a first regulating bearing configured to regulate a gap with the moving member with respect to a first direction and a second regulating bearing configured to regulate a gap with the moving member with respect to a second direction different from the first direction.

The moving device may further include a regulating member, and the gap between the regulating bearing and the moving member may become larger or smaller according to a rotation direction of the regulating member.

The housing may include a through hole provided at a position corresponding to the regulating bearing, and the regulating member may be inserted into the through hole and the regulating bearing may be configured to move forward or backward according to the direction of rotation of the regulating member.

The moving device may further include a fixed bearing installed in the housing and configured to assist the upward and downward movement of the moving member with the regulating bearing.

The moving member may include a contact portion provided on an outer surface of the moving member to come into contact with the regulating bearing or the fixed bearing, and the contact portion may be provided to be flat.

The housing may include a first surface and a second surface that face to each other, and the regulating bearing may be installed on the first surface and the fixed bearing may be installed on the second surface.

The contact portion may include a material having higher corrosion resistance and higher strength than the moving member.

The moving device may further include an auxiliary bearing installed on the moving member and configured to assist the movement of the moving member by coming into rolling contact with an inner surface of the housing.

The regulating bearing and the auxiliary bearing may include a roller bearing.

The direction of a reaction force generated when the regulating bearing comes into contact with the moving member and the direction of a reaction force generated when the auxiliary bearing comes into contact with the housing may be opposite to each other.

The moving device may further include an upper stopper and a lower stopper configured to determine an up and down movement range of the moving member.

The upper stopper and the lower stopper each may include a buffer member configured to buffer impact and noise when colliding with a counterpart.

The moving device may further include a driving member to provide a driving force so that the moving member moves in an upward direction, and the driving member may include any one of a gas cylinder, a gas spring, and an electric hydraulic motor.

Another aspect of the present disclosure provides an ultrasonic imaging apparatus including a moving device configured to connect a control panel and a main body and to move the control panel in the upward and downward directions, wherein the moving device includes a housing, a moving member configured to be movable with respect to the housing in the upward and downward directions, a regulating bearing installed in the housing and configured to come into rolling contact with an outer surface of the moving member and to regulate a gap with the moving member, and an auxiliary bearing installed on the moving member and configured to come into rolling contact with an inner surface of the housing.

The moving device may include at least two of the regulating bearings to regulate a gap with the moving member with respect to a first direction and a gap with the moving member with respect to a second direction different from the first direction. The moving device may further include a regulating member, and the gap between the regulating bearing and the moving member may become larger or smaller according to a rotation direction of the regulating member.

The moving member may include a contact portion provided on the outer surface of the moving member to come into contact with the regulating bearing, and the contact portion may be provided to be flat.

The contact portion may include a material having higher corrosion resistance and higher strength than the moving member.

The regulating bearing and the auxiliary bearing may include a roller bearing.

Advantageous Effects

The ultrasonic imaging apparatus according to the present disclosure can improve user convenience by reducing shaking and noise when a control panel moves up and down.

Further, the ultrasonic imaging apparatus according to the present disclosure can precisely move by reducing a clearance while having a simple structure.

MODE OF THE INVENTION

Hereinafter an ultrasonic imaging apparatus according to embodiments of the present disclosure will be described in detail with reference to the accompanying drawings.

Figure 1:
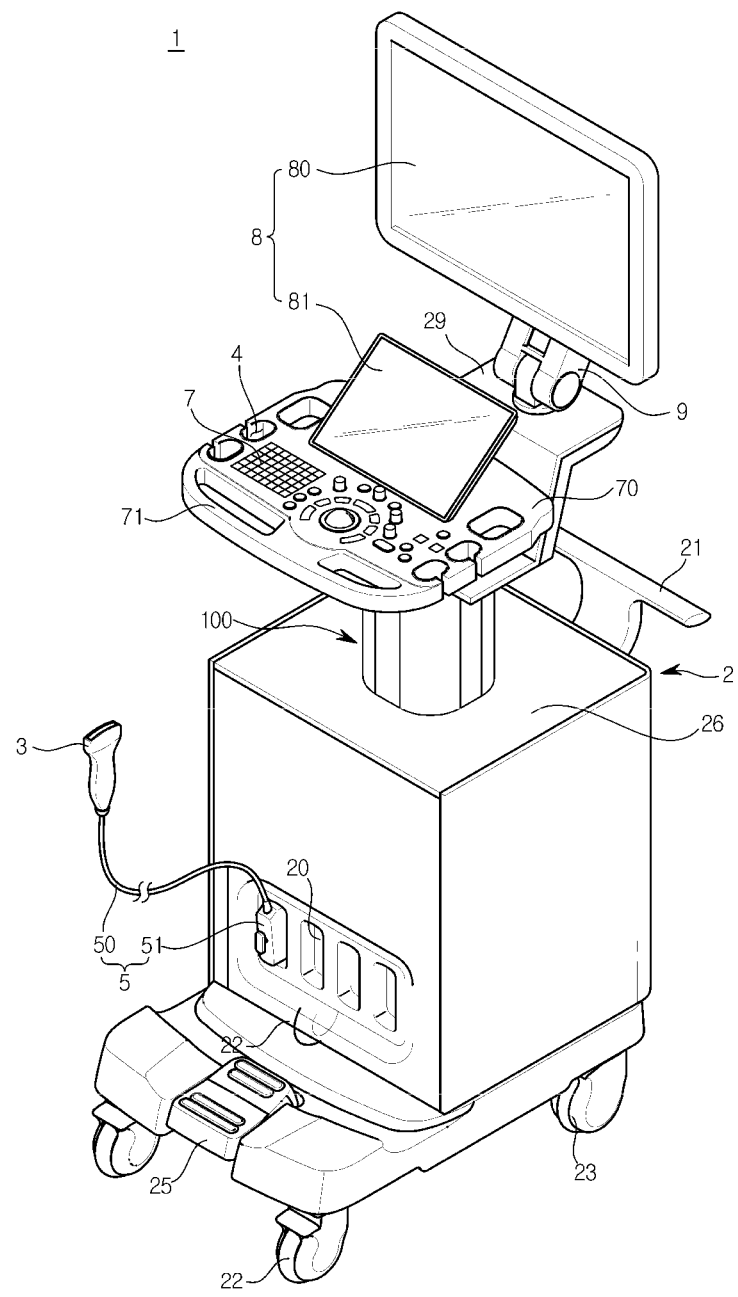
FIG. 1 is a perspective view of an ultrasonic imaging apparatus according to an embodiment of the present disclosure.

FIG. 1 is a perspective view of an ultrasonic imaging apparatus according to an embodiment of the present disclosure.

Referring to FIG. 1, an ultrasonic imaging apparatus 1 according to an embodiment of the present disclosure includes a main body 2, an ultrasonic probe 3, a controller 7, and a display member 8. The display member 8 may include a main display 80 and an auxiliary display 81.

The display member 8 may display an ultrasonic image obtained in an ultrasonic diagnostic process. In addition, the display member 8 may display an application related to the operation of the ultrasonic imaging apparatus 1. For example, the main display 80 may display ultrasonic images obtained in an ultrasonic diagnostic process, and the auxiliary display 81 may display matters related to the operation of the ultrasonic imaging apparatus 1.

The main display 80 or the auxiliary display 81 may be implemented as a cathode ray tube (CRT) or a liquid crystal display (LCD). The main display 80 or the auxiliary display 81 may be coupled to the main body 2 or may be separated from the main body 2.

The ultrasonic imaging apparatus 1 may further include a moving unit 9. The moving unit 9 may connect the main body 2 and the display member 8. The moving unit 9 may be configured to allow the display member 8 to be moved from the main body 2. By means of the moving unit 9, the display member 8 may be disposed in a state of being spaced apart from the main body 2.

The main body 2 may be provided with the controller 7. The controller 7 may be provided in the form of a keyboard, a button, a dial, a foot switch, or a foot pedal. In a case where the controller 7 is a keyboard, the controller 7 may be provided at an upper portion of the main body 2. In a case where the controller 7 is a foot switch or a foot pedal, the controller 7 may be provided at a lower portion of the main body 2. An inspector may control the operation of the ultrasonic imaging apparatus 1 through the controller 7.

The controller 7 may be provided by having a keyboard, a button, a dial, and the like on a control panel 70. The control panel 70 may be mounted to the main body 2. A handle 71 may be provided on one side of the control panel 70. A user may move the ultrasonic imaging apparatus 1 by holding the handle 71 and applying a force.

The ultrasonic probe 3 may be connected to the main body 2 by a connection member 5. The connection member 5 includes a cable 50 and a connector 51. The ultrasonic probe 3 may be provided on one side of the cable 50 and the connector 51 may be provided on the other side of the cable 50. The connector 51 may be detachably mounted on a connection portion 20 provided on the main body 2. Accordingly, the ultrasonic probe 3 may be connected to the main body 2.

A rest portion 4 may be provided on one side of the ultrasonic imaging apparatus 1 so that the ultrasonic probe 3 may be rested in the main body 2. When the ultrasonic imaging apparatus 1 is not used, the inspector may put and store the ultrasonic probe 3 in the rest portion 4. As an example, the rest portion 4 may be provided on the control panel 70 in the form of a hole through which a handle portion of the ultrasonic probe 3 may penetrate. The ultrasonic probe 3 may be rested in the panel 70 by being inserting into the hole formed on the control panel 70. As another example, the rest portion 4 may be provided in the form of a holder mounted on the main body 2. The ultrasonic probe 3 may be inserted into and rested in the holder.

The main body 2 may be provided with a handle 21 and the handle 71 on a from side and a rear side thereof so that the user may move the ultrasonic imaging apparatus 1. The handles 21 and 71 may include the first handle 71 provided on the front side of the main body 2 and the second handle 21 provided on the rear side of the main body 2. The first handle 71 may be provided on one side of the control panel 7. The second handle 21 may be provided to protrude from the rear of the main body 2.

The main body 2 may be provided with a plurality of casters 22 and 23 for moving the ultrasonic imaging apparatus 1. The casters 22 and 23 may be aligned so as to cause the main body 2 to travel in a specific direction (alignment movement mode), may be arranged so as to cause the main body 2 to freely move (free movement mode), or may be locked so as to cause the main body 2 to stop at a specific position (stop mode).

The casters 22 and 23 may include the first casters 22 and the second casters 23. When the direction in which the controller 7 and the display member 8 are positioned is referred to as the front and the direction opposite thereto is referred to as the rear, the first casters 22 may be positioned on the front side of the main body 2, and the second casters 23 may be positioned on the rear side of the main body 2. The first casters 22 may be provided on both the left and right sides of the front side of the main body 2, respectively. The second casters 23 may be provided on both the left and right sides of the rear side of the main body 2, respectively, so as to correspond to the first casters 22.

The main body 2 may be provided with an operation member 25 capable of controlling the first and second casters 22. The operation member 25 may be provided in the form of a foot pedal as illustrated in FIG. 1, or may be provided in the form of a button, a dial, or the like. The user may grasp the first handle 71 and move or stop the ultrasonic imaging apparatus 1 after pressing and operating the foot pedal 25 with the foot.

Although not specifically illustrated in FIG. 1, the ultrasonic imaging apparatus 1 according to an embodiment of the present disclosure includes a moving device 100 provided to move the control panel 70 in the upward and downward directions.

Hereinafter the moving device 100 according to an embodiment of the present disclosure will be described in detail.

Figure 2:
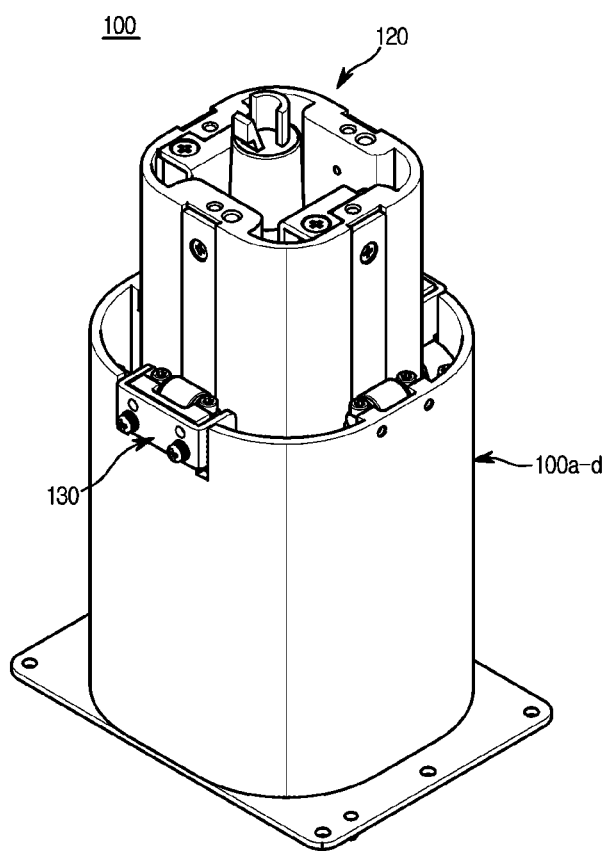
FIG. 2 is a perspective view of a moving device separated from the ultrasonic imaging apparatus according to an embodiment of the present disclosure.
Figure 3:
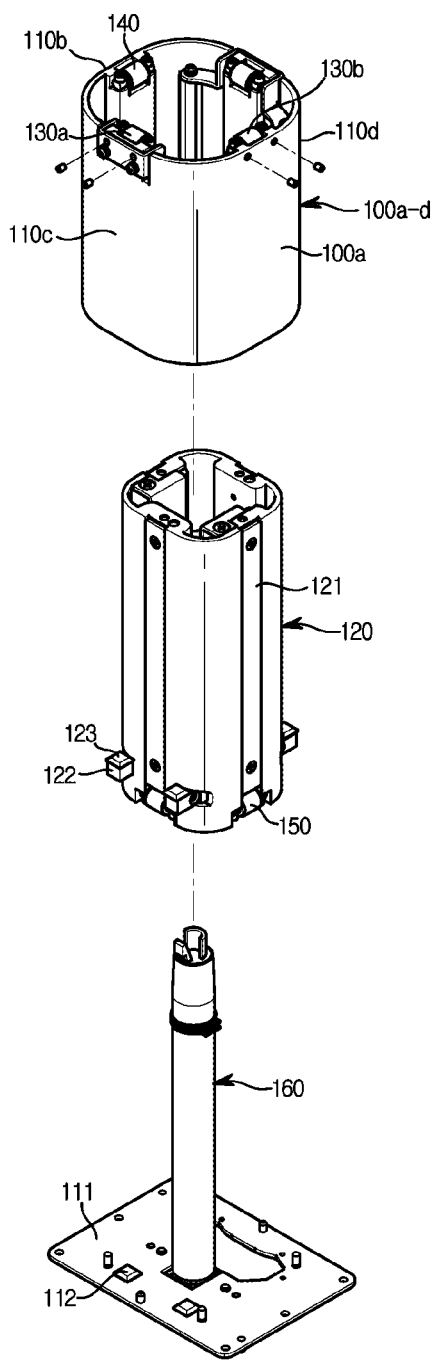
FIG. 3 is an exploded perspective view of the moving device illustrated in FIG.

FIG. 2 is a perspective view of a moving device separated from the ultrasonic imaging apparatus according to an embodiment of the present disclosure, and FIG. 3 is an exploded perspective view of the moving device illustrated in FIG. 2.

As illustrated in FIG. 2, the moving device 100 may include a housing 110 fixed to the main body 2, a moving member 120 provided to be movable with respect to the housing 110 in the upward and downward directions, and a regulating bearing 130 installed in the housing 110 to come into rolling contact with an outer surface of the moving member 120.

The housing 110 is configured to be fixed to the main body 2 and may accommodate the moving member 120 therein. The regulating bearing 130 may be provided at an upper portion of the housing 110.

At least a portion of the moving member 120 may be disposed inside the housing 110, and the moving member 120 may be provided to be movable with respect to the housing 110 in the upward and downward directions. The control panel 70 may be coupled to an upper portion of the moving member 120 to be moved in the upward and downward directions as the moving member 120 moves.

According to the spirit of the present disclosure, the moving device 100 may include at least two of the regulating bearings 130. The reason why the moving device 100 includes two or more of the regulating bearings 130 is to regulate clearances with the moving member 120 with respect to two directions perpendicular to each other. Detailed explanation thereof will be described later.

According to an embodiment of the present disclosure, the moving device 100 may include a first regulating bearing 130a and a second regulating bearing 130b.

The housing 110 may include a front surface 110a, a rear surface 110b, and opposite side surfaces 110c and 110d. An inserting space into which the moving member 120 may be inserted may be formed inside four of the surfaces 110a, 110b, 110c, and 110d.

The first regulating bearing 130a may be installed on the side surface 110c. The second regulating bearing 130b may be installed on the front surface 110a. The side surface 110c and the front surface 110a on which the first regulating bearing 130a and the second regulating bearing 130b are installed, respectively, may be provided to be perpendicular to each other. Accordingly, a clearance with the moving member 120 with respect to a first direction may be regulated through the first regulating bearing 130a, and a clearance with the moving member 120 with respect to a second direction perpendicular to the first direction may be regulated through the second regulating bearing 130b. However, as will be described later, three or more of the regulating bearings 130 may be provided. In this case, the first direction and the second direction may not be perpendicular to each other.

According to an embodiment of the present disclosure, the moving device 100 may include the regulating bearing 130 and a fixed bearing 140 for assisting the up and down movement of the moving member 120 with the regulating bearing 130.

The fixed bearing 140 may be provided basically similar to the regulating bearing 130. However, the fixed bearing 140, unlike the regulating bearing 130, does not have a function of regulating the distance with the moving member 120 by moving forward or backward. This is because only two of the regulating bearings 130 may regulate the spacing for two axes that are perpendicular to each other.

The fixed bearing 140 and the regulating bearing 130 may be disposed to face each other. For example, the first regulating bearing 130a may be installed on the side surface 110c of the housing 110 and the fixed bearing 140 may be installed on the other side surface 110d of the housing 110. FIG. 3 illustrates that the regulating bearing 130 and the fixed bearing 140 are disposed to face each other, but the present disclosure is not limited thereto. The first regulating bearing 130a may be installed at one side of the side surface 110c and the fixed bearing 140 may be installed at one side of the other side surface 110d so as not to face the first regulating bearing 130a.

Likewise, the second regulating bearing 130b may be installed on the front surface 110a of the housing 110 and the fixed bearing 140 may be installed on the rear surface 110b of the housing 110.

However, the present disclosure is not limited thereto. The fixed bearing 140 is not an essential configuration, and the regulating bearing 130 may be installed instead of the fixed bearing 140. Accordingly, the moving device 100 may include four of the regulating bearings 130 installed on four of the surfaces of the housing 110, respectively.

The moving member 120 may be inserted into the inside of the housing 110. The moving member 120 may move in the upward and downward directions by coining into rolling contact with the regulating bearing 130 and the fixed bearing 140.

The moving member 120 may include a contact portion 121 in an area coming into contact with the regulating bearing 130 and the fixed bearing 140.

The contact portion 121 may be provided to be flat so that the regulating bearing 130 and the fixed bearing 140 may be in surface contact. In addition, the contact portion 121 may be formed of a material different from the moving member 120 so as not to be easily worn or deformed by the contact with the regulating bearing 130 or the fixed bearing 140. To this end, the contact portion 121 may be formed of a stronger and harder material than the moving member 120. In addition, because the moving member 120 may be exposed to the outside according to the up and down movement, it is appropriate that the contact portion 121 is formed of a material having a high corrosion resistance.

An auxiliary bearing 150 may be provided at a lower portion of the moving member 120 to come into rolling contact with an inner surface of the housing 110.

The auxiliary bearing 150, the regulating bearing 130 and the fixed bearing 140 may be provided as roller bearings. Accordingly, the bearings 130, 140, and 150 of the present disclosure have a much greater load bearing capability compared to the ball bearings, and thus may stably support the moving member 120 and the housing 110.

As in the case of the regulating bearing 130 and the fixed bearing 140, four of the auxiliary bearings 150 may be provided. Although there is no particular limitation on the number of the auxiliary bearings 150, it is appropriate that four of bearings are provided to come into rolling contact with respect to four of the surfaces 110a, 110b, 110c, and 110d of the housing 110, respectively.

A first stopper 122 may be provided on the outer surface of the moving member 120. A buffer member 123 may be disposed on an upper surface of the first stopper 122 to buffer impact and noise when colliding with a counterpart. For example, the buffer member 123 may be formed of a rubber material.

The housing 110 may be provided in a form in which an upper surface and a lower surface thereof are open. A housing cover 111 may be provided to cover the open lower surface of the housing 110. The housing cover 111 may include a second stopper 112 for determining the lowest position of the moving member 120 and for buffering impact and noise when colliding with the moving member 120. The second stopper 112 may be formed of the same material as the buffer member 123. Therefore, the second stopper 112 may be formed of a rubber material.

A driving member 160 may be provided inside the moving member 120. The driving member 160 may provide a driving force to the moving member 120 when the moving member 120 moves up and down. According to an embodiment of the present disclosure, the driving member 160 may be provided as a gas cylinder. Alternatively, the driving member 160 may include a gas spring and an electric hydraulic motor.

Figure 4:
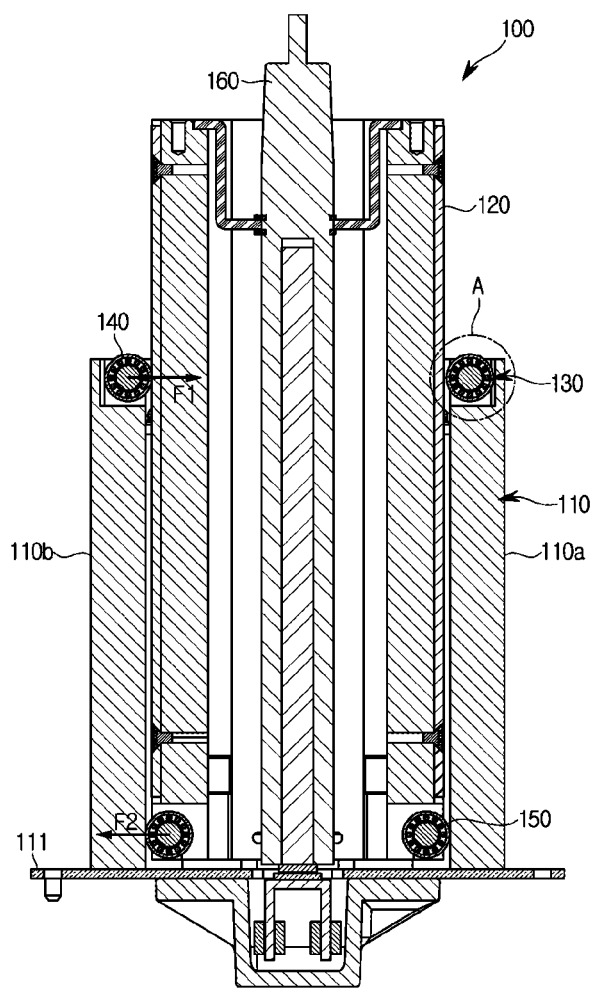
FIG. 4 is a side cross-sectional view of the moving device illustrated in FIG. 2.
Figure 5:
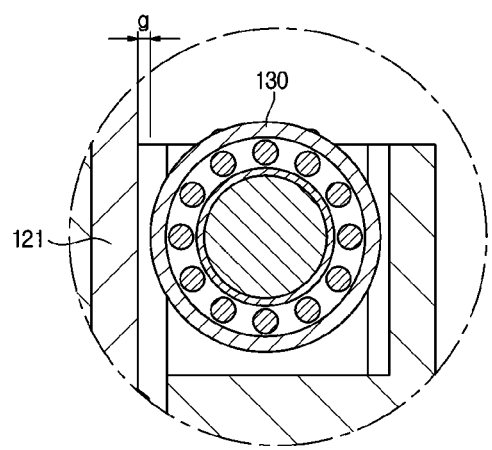
FIGS. 5 and 6 are enlarged views of a portion A of FIG. 4.
Figure 6:
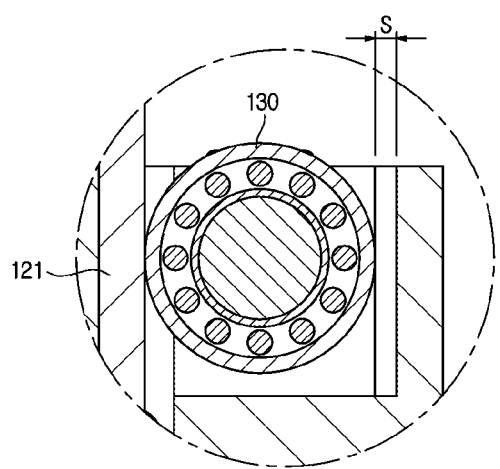

FIG. 4 is a side cross-sectional view of the moving device illustrated in FIG. 2, and FIGS. 5 and 6 are enlarged views of a portion A of FIG. 4.

As illustrated in FIG. 4, the regulating bearing 130 may be provided to come into rolling contact with the contact portion 121 provided on the outer surface of the moving member 120. Likewise, the fixed bearing 140 may be provided to come into rolling contact with the contact portion 121. With this configuration, the moving member 120 may move up and down relatively with respect to the housing 110.

The moving member 120 may be difficult to stably move with respect to the housing 110 only by supporting the moving member 120 by the contact of the regulating bearing 130 and the fixed bearing 140 with the outer surface of the moving member 120. Therefore, according to the spirit of the present disclosure, the auxiliary bearing 150 may be provided the lower portion of the moving member 120 to come into rolling contact with the inner surface of the housing 110.

With this configuration, the regulating bearing 130 or the fixed bearing 140 and the auxiliary bearing 150 may provide reaction forces in opposite directions with respect to the moving member 120 and the housing 110, respectively. As illustrated in FIG. 4, the regulating bearing 130 or the fixed bearing 140 exerts a reaction force in a direction F1 toward the moving member 120, and the auxiliary bearing 150 exerts a reaction force in a direction F2, which is opposite to the direction F1, toward the housing 110. Because the housing 110 and the moving member 120 are supported by reaction forces in opposite directions, the moving member 120 may be stably supported within the housing 110.

Hereinafter a method of regulating a clearance of the regulating bearing according to the spirit of the present disclosure will be described in detail.

As illustrated in FIG. 5, the regulating bearing 130 and the contact portion 121 may be maintained in a non-contact state. That is, there may be a clearance g between the regulating bearing 130 and the contact portion 121. This clearance is a tolerance necessary for assembling the moving member 120 into the housing 110, and is necessary because when there is no tolerance or the tolerance is too small, the moving member 120 may not be inserted into the housing 110.

After the moving member 120 is inserted into the housing 110, as illustrated in FIG. 6, the regulating bearing 130 and the contact portion 121 may be maintained in contact with each other. That is, the clearance between the moving member 120 and the regulating bearing 130 may be minimized. In this case, a gap s is generated between the regulating bearing 130 and the housing 110. The gap s is the maximum movement distance that the regulating bearing 130 may move forward or backward, and the maximum tolerance that the regulating bearing 130 may provide when the moving member 120 and the housing 110 are assembled.

Figure 7:
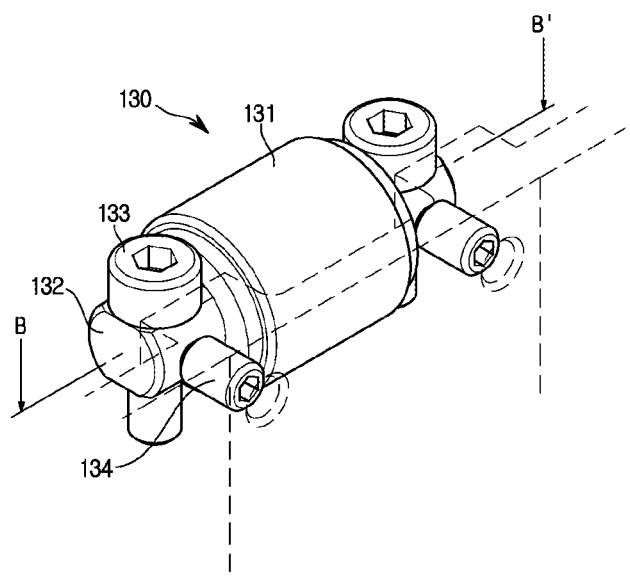
FIG. 7 is a perspective view of a regulating bearing and a regulating member in the ultrasonic imaging apparatus according to an embodiment of the present disclosure.
Figure 8:
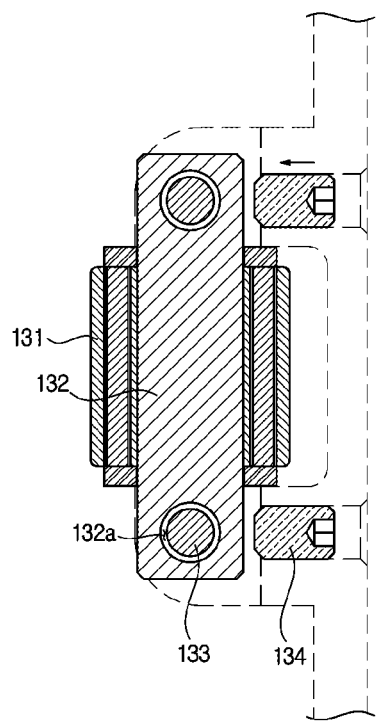
FIGS. 8 and 9 are cross-sectional views of the regulating bearing and the regulating member illustrated in FIG. 7 and illustrate the operation of the regulating bearing.
Figure 9:
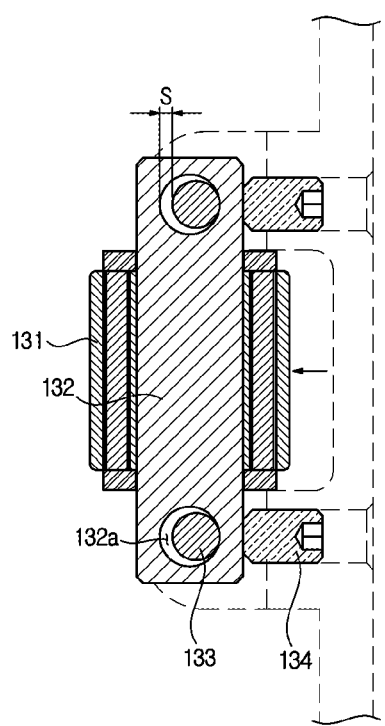

FIG. 7 is a perspective view of a regulating bearing and a regulating member in the ultrasonic imaging apparatus according to an embodiment of the present disclosure, and FIGS. 8 and 9 are cross-sectional views of the regulating bearing and the regulating member illustrated in FIG. 7 and illustrate the operation of the regulating bearing.

As illustrated in FIG. 7, the regulating bearing 130 may include a rolling portion 131 provided to rotate by the contact with the moving member 120, a shaft 132 penetrating through the rolling portion 131 to be a rotation axis of the rolling portion 131, shaft holes 132a (refer to FIG. 8) formed on opposite ends of the shaft 132, a fastening portion 133 inserted into each of the shaft holes 132a to fix the shaft 132 to the housing 110, and a regulating member 134 for moving the position of the regulating bearing 130.

As illustrated in FIGS. 8 and 9, when the regulating member 134 does not come into contact with the shaft 132, the shaft 132 may move forward or backward within the range of the gap s. This is because the shaft hole 132a is slightly larger than the fastening portion 133 inserted into the shaft hole 132a, so that a clearance is generated by the gap s which is a difference value between the inner diameter of the shaft hole 132a and the outer diameter of the fastening portion 133. When the shaft 132 is movable, a maximum tolerance corresponding to the gap s exists between the moving member 120 and the housing 110, and thus the moving member 120 may be easily assembled to the housing 110.

As illustrated in FIG. 9, in order to minimize the clearance between the moving member 120 and the housing 110, the regulating member 134 may be moved toward the shaft 132. The regulating member 134 may be moved toward the shaft 132 until the rolling portion 131 comes into contact with the contact portion 121, that is, the clearance is minimized. The user may regulate the clearance between the moving member 120 and the regulating bearing 130 by adjusting the position of the regulating member 134.

The regulating member 134 may be a screw coupled to a through hole (not shown) provided in the housing 110 by rotation. In this case, threads may be formed on an inner circumferential surface of the through hole. However, the type of the regulating member 134 is not limited, and may include a configuration capable of moving forward or backward by various methods such as rotation.

Figure 10:
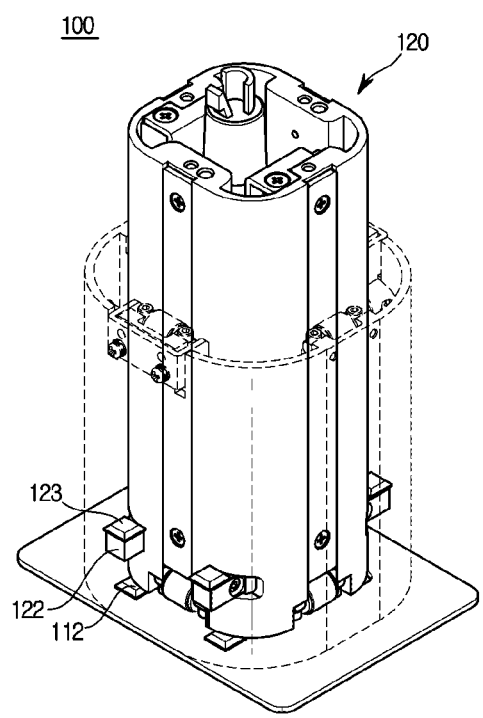
FIG. 10 is a view illustrating the moving device when a moving member moves downward to the maximum in the ultrasonic imaging apparatus according to an embodiment of the present disclosure.
Figure 11:
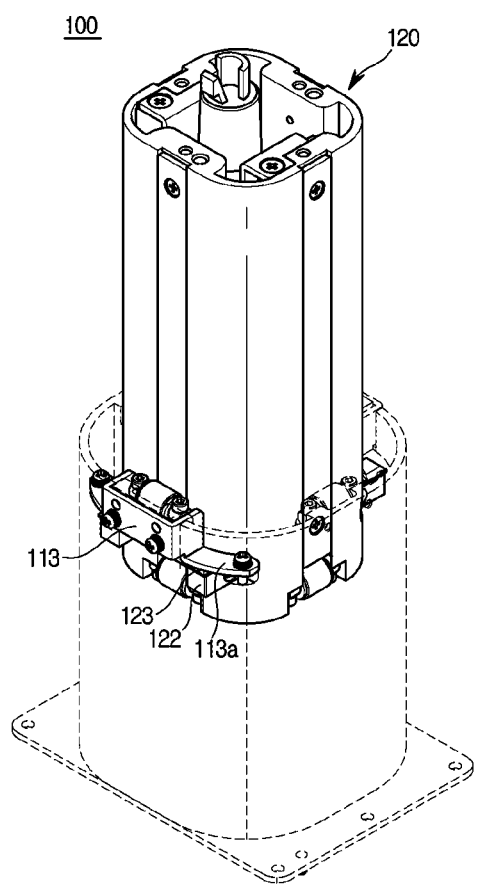
FIG. 11 is a view illustrating the moving device when the moving member moves upward to the maximum in the ultrasonic imaging apparatus according to an embodiment of the present disclosure.

FIG. 10 is a view illustrating the moving device when a moving member moves downward to the maximum in the ultrasonic imaging apparatus according to an embodiment of the present disclosure, and FIG. 11 is a view illustrating the moving device when the moving member moves upward to the maximum in the ultrasonic imaging apparatus according to an embodiment of the present disclosure.

As illustrated in FIG. 10, when the moving member 120 is at the lowest position, a lower surface of the moving member 120 may come into contact with the second stopper 112. In other words, when the lower surface of the moving member 120 comes into contact with the second stopper 112, the moving member 120 may no longer move downward. That is, the second stopper 112 determines the lowest position of the moving member 120. The second stopper 112 may be disposed on one side of the housing cover 111. The second stopper 112 may be formed of a rubber material in order to buffer the impact and noise generated when the moving member 120 descends at a high speed and contacts the second stopper 112.

As illustrated in FIG. 11, when the moving member 120 is at the highest position, the first stopper 122 provided on the side surface of the moving member 120 may come into contact with a bracket 113 mounted on the housing 110. In other words, when the first stopper 122 comes into contact with the bracket 113, the moving member 120 may no longer move upward. That is, the first stopper 122 and the bracket 113 determine the highest position of the moving member 120.

More specifically, the bracket 113 may include a flat portion 113a provided to come into contact with the first stopper 122. When the moving member 120 moves upward and the first stopper 122 comes into contact with the flat portion 113a, the upward movement of the moving member 120 is limited.

The buffer member 123 may be provided on an upper surface of the first stopper 122 in order to buffer the impact and noise generated when the moving member 120 ascends at a high speed and contacts the first stopper 122. The buffer member 123 may be formed of a rubber material or various materials capable of absorbing impact and noise.

Although not shown in the drawings, according to the spirit of the present disclosure, the regulating bearing 130, the fixed bearing 140 and the auxiliary bearing 150 may be provided as pinion gears. In this case, the contact portion 121 may be provided as a rack gear corresponding to the pinion gear. In contrast, the regulating bearing 130, the fixed bearing 140 and the auxiliary bearing 150 may be provided as the rack gears, and the contact portion 121 may be provided as the pinion gear.

Figure 12:
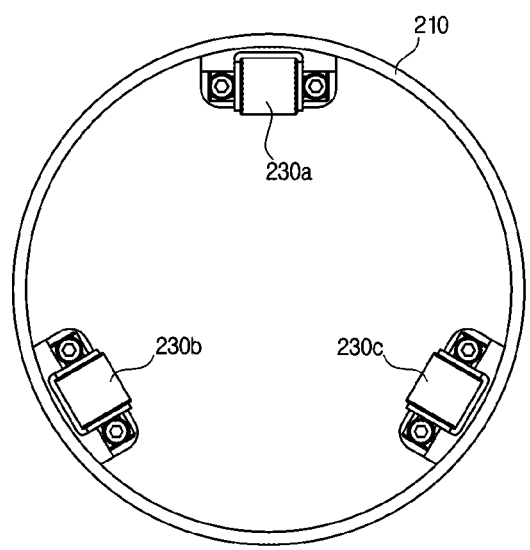
FIG. 12 is a plan view of a moving device separated from an ultrasonic imaging apparatus according to another embodiment of the present disclosure.

FIG. 12 is a plan view of a moving device separated from an ultrasonic imaging apparatus according to another embodiment of the present disclosure.

As illustrated in FIG. 12, a housing 210 may include three of regulating bearings. That is, the regulating bearings may include a first regulating bearing 230a, a second regulating bearing 230b, and a third regulating bearing 230c.

The first regulating bearing 230a may regulate a clearance with a moving member (not shown) with respect to a first direction, the second regulating bearing 230b may regulate a clearance with the moving member with respect to a second direction different from the first direction, and the third regulating bearing 230c may regulate a clearance with the moving member with respect to a third direction different from the first direction and the second direction.

As illustrated in FIG. 12, when three of the regulating bearings are provided, the first regulating bearing 230a, the second regulating bearing 230b, and the third regulating bearing 230c may be arranged at intervals of 120 degrees. However, the present disclosure is not limited thereto, and the angle between the plurality of regulating bearings may vary according to design specifications, and the number of regulating bearings may also be greater than three.

Modifications or variations are possible within the scope of equivalents and/or within the skill or knowledge of the art. The described embodiments illustrate the best state for implementing the technical idea of the present disclosure, and various modifications required in the specific application field and use of the present disclosure are possible. Therefore, the detailed description of the present disclosure is not intended to limit the invention to the disclosed embodiments. Also, the appended claims should be construed to include other embodiments.

The invention claimed is:
1. An ultrasonic imaging apparatus comprising:
a main body;
a probe connected to the main body to irradiate and receive ultrasonic signals and to transmit the ultrasonic signals to the main body;

a control panel configured to control the main body or the probe; and a moving device configured to connect the control panel and the main body and to move the control panel with respect to the main body in the upward and downward directions, wherein the moving device includes:
- a housing fixed to the main body;
- a moving member configured to be movable with respect to the housing in the upward and downward directions;
- a regulating bearing installed in the housing and configured to assist the upward and downward movement of the moving member by coming into rolling contact with the moving member and to regulate a gap with the moving member, and wherein the regulating bearing includes a first regulating bearing configured to regulate a gap with the moving member with respect to a first direction and a second regulating bearing configured to regulate a gap with the moving member with respect to a second direction different from the first direction.

2. The ultrasonic imaging apparatus according to claim 1, wherein the moving device further includes a regulating member, and the gap between the regulating bearing and the moving member becomes larger or smaller according to a rotation direction of the regulating member.

3. The ultrasonic imaging apparatus according to claim 2, wherein the housing includes a through hole provided at a position corresponding to the regulating bearing, and the regulating member is inserted into the through hole and the regulating bearing is configured to move forward or backward according to the direction of rotation of the regulating member.

4. The ultrasonic imaging apparatus according to claim 1 wherein the moving device further includes a fixed bearing installed in the housing and configured to assist the upward and downward movement of the moving member with the regulating bearing.

5. The ultrasonic imaging apparatus according to claim 4, wherein the moving member includes a contact portion provided on an outer surface of the moving member to come into contact with the regulating bearing or the fixed bearing, and the contact portion is provided to be flat.

6. The ultrasonic imaging apparatus according to claim 5, wherein the contact portion includes a material having higher corrosion resistance and higher strength than the moving member.

7. The ultrasonic imaging apparatus according to claim 4, wherein the housing includes a first surface and a second surface that face to each other, and the regulating bearing is installed on the first surface and the fixed bearing is installed on the second surface.

8. The ultrasonic imaging apparatus according to claim 1, wherein the moving device further includes an auxiliary bearing installed on the moving member and configured to assist the movement of the moving member by coming into rolling contact with an inner surface of the housing.

9. The ultrasonic imaging apparatus according to claim 8, wherein the regulating bearing and the auxiliary bearing include a roller bearing.

10. The ultrasonic imaging apparatus according to claim 8, wherein the direction of a reaction force generated when the regulating bearing comes into contact with the moving member and the direction of a reaction force generated when the auxiliary bearing comes into contact with the housing are opposite to each other.

11. The ultrasonic imaging apparatus according to claim 1, wherein the moving device further includes both an upper stopper and a lower stopper configured to determine an up and down movement range of the moving member.

12. The ultrasonic imaging apparatus according to claim 11, wherein the upper stopper and the lower stopper each include a buffer member configured to buffer impact and noise when colliding with a counterpart.

13. The ultrasonic imaging apparatus according to claim 1, wherein the moving device further includes a driving member to provide a driving force so that the moving member moves in an upward direction, and the driving member includes any one of a gas cylinder, a gas spring, and an electric hydraulic motor.

* * * * *